United States Patent [19]

Fiard et al.

[11] Patent Number: 5,290,751

[45] Date of Patent: Mar. 1, 1994

[54] PLANT-PROTECTION SUSPENSIONS COMPRISING SUCROGLYCERIDES

[75] Inventors: Jean-Francois Fiard; Marie-Luce Prevotat, both of Paris, France

[73] Assignee: Rhone-Poulenc Chimie, Courbevoie, France

[21] Appl. No.: 804,322

[22] Filed: Dec. 9, 1991

[51] Int. Cl.$^5$ .............................................. A01N 25/30
[52] U.S. Cl. .................................. 504/116; 424/405; 514/975
[58] Field of Search ..................... 71/93, 120, DIG. 1; 504/116; 424/405; 514/975

[56] References Cited

U.S. PATENT DOCUMENTS

| | | | |
|---|---|---|---|
| 3,882,243 | 5/1975 | Maeda et al. | 424/312 |
| 4,061,770 | 12/1977 | Marks | 71/DIG. 1 |
| 4,461,641 | 7/1984 | Abildt et al. | 71/93 |
| 4,692,187 | 9/1987 | Kiehs et al. | 71/120 |

FOREIGN PATENT DOCUMENTS

| | | |
|---|---|---|
| 1189344 | 6/1985 | Canada . |
| 82437 | 6/1983 | European Pat. Off. . |
| 88049 | 9/1983 | European Pat. Off. . |
| 373837 | 9/1983 | European Pat. Off. . |
| 91331 | 10/1983 | European Pat. Off. . |
| 341126 | 11/1989 | European Pat. Off. . |
| 0373837 | 6/1990 | European Pat. Off. . |
| 2241667 | 3/1973 | Fed. Rep. of Germany . |
| 1538342 | 9/1968 | France . |
| 423442 | 4/1967 | Switzerland . |

OTHER PUBLICATIONS

Patent Abstracts of Japan, vol. 5 (45) 56-1845.

*Primary Examiner*—Richard E. Raymond
*Assistant Examiner*—S. Mark Clardy
*Attorney, Agent, or Firm*—Finnegan, Henderson, Farabow, Garrett & Dunner

[57] ABSTRACT

The present invention relates to a new aqueous plant-protection suspensions. It more particularly relates to a concentrated aqueous suspension of solid active substance having a melting point greater than or equal to 45° C. and which is substantially insoluble in water. The suspension comprises a solid active substance; sucroglycerides; at least one compound selected from an alkoxylated triglyceride, an alkoxylated fatty acid, a sorbitan ester, and an alkoxylated sorbitan ester; a wetting agent, when required; and water.

The suspensions prepared in accordance with the present invention can be diluted to the concentration desired by the user without problems of flocculation or sedimentation.

29 Claims, No Drawings

PLANT-PROTECTION SUSPENSIONS COMPRISING SUCROGLYCERIDES

This application is related to copending applications Ser. No. 07/804,327, filed Dec. 9, 1991 and Ser. No. 07/820,416, filed Jan. 15, 1992.

The present invention relates to new aqueous plant-protection suspensions. Active substances such as insecticides, germicides, herbicides, fungicides, acaricides, nematicides, molluscicides, rodenticides, attractants, repellents, and combinations of these compounds, are generally insoluble in water. They can normally be used in solutions with organic solvents, wherein these solutions are emulsified in water at the time of their use. However, the use of solvents, such as xylenes or kerosine, presents obvious problems of environmental pollution.

Another mode of preparation of compositions of active substances consists of fluid aqueous dispersions, or "flowable" dispersions, which are diluted at the time of their use. These aqueous dispersions contain one or more surface-active agents.

Increasingly, more serious consideration is being given to the various problems of environmental pollution. Plant-protection compositions which are less and less toxic are being sought.

The present invention provides an alternative to environmentally harmful plant-protection suspensions through the use of a surface-active system which comprises, at least in part, non-toxic, non-irritant and biodegradable compounds. The emulsive and dispersive nature of sucroglycerides is known for preparing dispersed aqueous systems of fatty substances. Sucroglycerides are mixtures of products obtained by transesterification of natural or synthetic triglycerides with sucrose. These mixtures include monoglycerides, diglycerides, small quantities of nonesterified triglycerides, monoesters and diesters of sucrose.

European patent application EP-A-0,091,331, which describes a process for the preparation of flowable sucroglycerides, also discloses that sucroglycerides have surface-active properties, which may be used for the preparation of emulsions of essential oils or recombined milk. Sucroglycerides may also be combined with lecithins and flowable oils.

Swiss patent CH 423,442 describes a process for the preparation of emulsions of oils or solid fatty substances in water, using sucroglycerides and a lecithin as an emulsifying system.

The present invention uses the dispersive ability of sucroglycerides for obtaining stable suspensions of active plant-protection substances. A concentrated aqueous suspension of a solid active substance, having a melting point greater than or equal to 45° C., is produced which is substantially insoluble in water. The suspension contains the active substance, sucroglycerides, at least one compound selected from an alkoxylated triglyceride, an alkoxylated fatty acid, a sorbitan ester, and an alkoxylated sorbitan ester, and water.

Preferably, a wetting agent is added to these suspensions. Particularly a wetting agent is added to the more concentrated suspensions, such as suspensions containing more than 30 % by weight of active substance per volume of aqueous suspension.

Preferably, the invention comprises a concentrated aqueous suspension of a solid active substance, wherein the solid active substance has a melting point greater than or equal to 45° C. and is significantly insoluble in water. The concentrated aqueous suspension contains the active substance, sucroglycerides, at least one selected from an alkoxylated triglyceride, an alkoxylated fatty acid, a sorbitan ester and an alkoxylated sorbitan ester, a wetting agent selected from anionic salts of surface-active agents, alkoxylated alcohols or phenols, silicone-based surface-active agents and fluorinated surface-active agents, and water.

As previously indicated, sucroglycerides are obtained from the transesterification of triglycerides with sucrose. In the present text, the term "sucroglycerides" is used in the plural to indicate that they are not composed of only one chemical compound. The triglycerides of saturated or unsaturated aliphatic acids with at least 4 carbon atoms are preferably used. Preferably, the acids from which the triglycerides are derived have 10 to 20 carbon atoms.

The preparation of the sucroglycerides may be carried out using synthetic triglycerides obtained by the reaction of glycerol and fatty acids. However, it is more useful from an economic point of view to use natural triglycerides. These natural triglycerides are mixtures of triglycerides.

Examples of natural triglycerides are lard, tallow, groundnut oil, butter oil, cottonseed oil, linseed oil, olive oil, palm oil, grape-seed oil, fish oil, soya-bean oil, castor oil, colza oil, copra oil, and coconut oil.

In the present invention, the sucroglycerides used are preferably obtained from palm oil, lard, copra oil, tallow, colza oil, and castor oil. They are either in liquid form such as sucroglycerides of colza oil or castor oil, or in the form of more or less thick pastes, which are distinguishable notably by their melting point:

sucroglycerides of lard 47° to 50° C.
sucroglycerides of tallow: 50° to 55° C.
sucroglycerides of palm oil: 55° to 58° C.
sucroglycerides of copra oil: 60° to 62° C.

A method of preparation of sucroglycerides is described in French patent 2,463,512.

The aqueous suspension may also contain a phospholipid in combination with the sucroglycerides. Examples of phospholipids are crude lecithins of plant or animal origin, such as soybean lecithin or egg-yolk lecithin, as well as any lecithin fraction.

The aqueous suspension preferably comprises from 0.1% to 5% by weight of sucroglycerides, or optionally sucroglycerides and phospholipid, relative to the total volume of the suspension, and preferably from 0.2% to 4% by weight/volume. When a phospholipid is present with the sucroglycerides, the weight ratio of sucroglycerides/phospholipid is preferably 3:1 to 1:3.

The active plant-protection substance used in the present invention is substantially insoluble in water, preferably its solubility in water at 20° C. is lower than 5 g/liter. Furthermore, the active substances used must be stable with respect to water.

Nonrestrictive examples of active substances which can be used in the suspensions in accordance with the present invention are deltamethrin, propham, tetramethrin, furalaxyl, heptachlor, propanil, oxadiazon, triflumizole, dimethamethrin, atrazine, diuron, neburon, linuron, isoproturon, simazine, ametryne, phenmedipham, and pendimethalin.

The suspensions in accordance with the present invention also comprise at least one compound selected from an alkoxylated triglyceride, an alkoxylated fatty acid, a sorbitan ester and an alkoxylated sorbitan ester, and preferably comprise at least one selected from ethoxylated triglycerides, ethoxylated fatty acids, sorbitan esters and ethoxylated sorbitan esters.

The ethoxylated triglycerides may be ethoxylated triglycerides of plant or animal origin such as lard, tallow, groundnut oil, butter oil, cottonseed oil, linseed oil, olive oil, palm oil, grape-seed oil, fish oil, soya-bean oil, castor oil, colza oil, copra oil or coconut oil.

The ethoxylated fatty acids are preferably ethoxylated esters of fatty acids such as oleic acid or stearic acid.

The sorbitan esters are preferably cyclic sorbitol esters of from $C_{10}$ to $C_{20}$ fatty acids such as lauric acid, stearic acid or oleic acid. These sorbitan esters may also be ethoxylated.

The term ethoxylated triglyceride, in the present invention, applies to products obtained by ethoxylation of a triglyceride with ethylene oxide, as well as to those obtained by transesterification of a triglyceride with a polyethylene glycol.

Similarly, the term ethoxylated fatty acid includes products obtained by ethoxylation of a fatty acid with ethylene oxide, as well as those obtained by esterification of a polyethylene glycol with a fatty acid.

The alkoxylated triglycerides, alkoxylated fatty acids, sorbitan esters and/or alkoxylated sorbitan esters preferably represent from 0.1% to 3% by weight per volume of the suspension and, more preferably, from 0.2% to 2.8% by weight/volume.

The wetting agent is a compound as defined in the standard NF T 73-000. Examples of wetting agents are anionic salts of surface-active agents, alkoxylated alcohols or alkoxylated alkylphenols which are represented by the following formulae:

$R_1$—$SO_3$—M
$R_2$—$SO_4$—M
$R_3$—$(EO)_n$—H
$R_3$—$(PO)_n$—H
$R_3$—$(EO—PO)_n$—H
$R_4$—COONa where:
$R_1$ represents
an alkylphenyl radical such as dodecylphenyl,
an alkyl radical such as dodecyl,
a 1,2-bis(octyloxycarbonyl) ethyl radical, preferably 1,2-bis (2-ethyl hexyloxycarbonyl) ethyl,
$R_2$ represents
an alkyl radical such as dodecyl,
an ethoxylated alkylphenol radical such as ethoxylated nonylphenol with 2 to 50 EO units,
an ethoxylated alkyl radical,
$R_3$ represents
an alkylaryl radical such as nonylphenyl, alkylnaphthyl,
an alkyl radical having from 8 to 20 carbon atoms, and preferably from 10 to 14 carbon atoms,
n is a number from 4 to 12,
$R_4$ represents an alkyl radical having 10 to 22 carbon atoms,
M represents Na, K, $NH_4$ or a triethanolammonium cation.

The wetting agent may also be a silicone-based surface-active agent such as a copolymer of (1) polydimethylsiloxane and (2) either a homopolymer of ethylene glycol or a copolymer of ethylene glycol and propylene glycol. The wetting agent may also be a fluorinated surface-active agent such as a compound containing a hydrophobic Or oleophobic perfluorocarbon linear chain and a hydrophilic region containing, for example, an acidic or neutralized sulphonic group, a carboxylic group or an ethoxylated alcohol radical.

The suspensions generally contain from 0.05% to 1% by weight of wetting agent relative to the total volume of the suspension, and preferably from 0.1% to 0.8% by weight/volume.

The aqueous suspensions generally contain from 30% to 90% by weight of active substance, relative to the total volume of the suspension and preferably from 40% to 85% by weight/volume.

The lower limit of this concentration range is not critical, and simply corresponds to the concentration which is normally considered to be the minimum for an economically viable storage of the suspensions.

In effect, the suspensions of the present invention are very stable with time and over a wide range of temperatures (for example between $-10°$ C. and $+54°$ C.). It is preferable from an economic point of view to store the suspensions in a concentrated form and to dilute them only at the time of use.

One of the advantages of the suspensions in accordance with the present invention is that the suspensions can be diluted to the concentration desired by the user, normally 0.5% to 2%, without problems of flocculation or sedimentation, to give dilute suspensions which remain stable during a period of use of about 24 hours.

Another advantage of these suspensions is that they possess some anti-foaming ability, derived from the sucroglycerides which they contain.

In the following illustrative examples of the invention, the quantities of the different constituents of the suspensions are given in grams for obtaining 1,000 $cm^3$ of suspension.

EXAMPLES

The procedure used was the same for the different examples.

First, the melted sucroglycerides were dispersed by mixing in water at 60° C., at 10% by weight/weight. This predispersion allowed the sucroglycerides to swell.

In the examples, the sucroglycerides were used in the form of a predispersion at 10% by weight/weight in water.

The ethoxylated triglyceride or ethoxylated fatty acid and the wetting agent were dissolved in water. The predispersion of the sucroglycerides, and also an anti-gelling compound when desired, was then added.

The active substance was then added in small fractions, while stirring, with an antifoaming agent when necessary.

The mixture was homogenized using a turbine, and then ground for a few minutes in a ball mill (glass beads of 1 mm in diameter) until an average particle size of 3 to 4 micrometers of active substance was obtained. Changes in the diameter of the particles were monitored using a granulometer.

A thickener (xanthan gum) was added when necessary and mixing was continued for about 30 minutes.

EXAMPLES 1 TO 4 AND COMPARATIVE TEST A

Preparation of aqueous suspensions of atrazine

Atrazine is a known herbicide, which has a melting point of 175° C. and a solubility in water at 25° C. of 0.028 g/l:

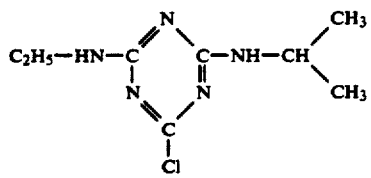

Following the procedure previously described, four aqueous suspensions of atrazine in accordance with the invention, and an aqueous suspension of atrazine not containing an ethoxylated triglyceride (comparative test A) were prepared. The respective compositions are shown in Table 1 below.

Table 1 also shows, for each of the suspensions:
- the average diameter of particles of the active substance (in micrometers),
- the value in seconds, for the measurement of the flow rate of the suspension (before addition of the thickener : xanthan gum) using a FORD Cup No. 4 (FC No. 4),
- the abbreviation EO corresponds to the oxyethylene unit in the formula of the triglycerides or ethoxylated fatty acids. The antifoam agent used is a polydiorgano-siloxane.

All the suspensions in Examples 1 to 4 were stable:
more than 2 months at 45° C. and
more than 2 months in the temperature cycle: 24 hours at +45° C., 24 hours at −5° C.

Dilution with water produced suspensions of 0.5% to 2% of active substance, without flocculation or sedimentation, during a period of use of about 24 hours.

The suspension according to the comparative test was also stable to storage, but it was difficult to grind and flocculation was observed on dilution with water.

TABLE 1

| Constituents of the suspension | Example 1 | Example 2 | Example 3 | Example 4 | Test A |
|---|---|---|---|---|---|
| Atrazine | 500 g | 500 g | 500 g | 500 g | 500 g |
| Sucroglycerides of castor oil, 10% in water | 150 g | 80 g | 100 g | 100 g | 150 g |
| Ethoxylated castor oil (about 33 EO) | 5 g | 4 g | 5 g | 5 g | 0 g |
| Ethoxylated copra oil (about 27 EO) | 0 g | 0 g | 0 g | 5 g | 0 g |
| Sodium dodecyl-benzenesulphonate | 0 g | 2 g | 0 g | 0.5 g | 2 g |
| Sodium lauryl sulphate | 2 g | 0 g | 2 g | 0 g | 0 g |
| Monopropylene glycol | 70 g | 80 g | 70 g | 70 g | 80 g |
| Xanthan gum, 2% in water | 50 g | 50 g | 50 g | 50 g | 50 g |
| Antifoam | 1 g | 1 g | 1 g | 1 g | 1 g |
| Water (sufficient quantity to make up to 1,000 cm$^3$) | 300 g | 450 g | 349 g | 345 g | 295 g |
| Average diameter of particles (in micrometers) | 3.1 | 3.1 | 2.8 | 3.2 | — |
| FC No. 4 | 17 s | 15 s | 35 s | 22 s | — |

EXAMPLES 5 to 8

Preparation of aqueous suspensions of atrazine

Following the procedure previously described, four aqueous suspensions of atrazine, whose respective compositions and properties are shown in Table 2 below (with the same abbreviations as in Table 1), were prepared.

As with the suspensions in Examples 1 to 4, all the suspensions in Examples 5 to 8 were stable:
more than 2 months at 45° C. and
more than 2 months in the temperature cycle: 24 hours at +45° C., 24 hours at −5° C.

By diluting with water, suspensions were produced with 0.5% to 2% of active substance, without flocculation or sedimentation, during a period of use of about 24 hours.

TABLE 2

| Constituents of the suspension | Example 5 | Example 6 | Example 7 | Example 8 |
|---|---|---|---|---|
| Atrazine | 500 g | 500 g | 500 g | 350 g |
| Sucroglycerides of tallow, 10% in water | 100 g | 50 g | 80 g | 50 g |
| Ethoxylated castor oil (about 33 EO) | 5 g | 4 g | 0 g | 5 g |
| Ethoxylated castor oil (about 18 EO) | 0 g | 0 g | 8 g | 0 g |
| Ethoxylated copra oil (about 27 EO) | 0 g | 0 g | 8 g | 0 g |
| Sodium dodecylbenzene-sulphonate | 0 g | 2 g | 2 g | 0 g |
| Sodium lauryl sulphate | 2 g | 0 g | 0 g | 2 g |
| Monopropylene glycol | 80 g | 80 g | 80 g | 80 g |
| Xanthan gum, 2% in water | 50 g | 50 g | 40 g | 60 g |
| Antifoam | 1 g | 1 g | 1 g | 1 g |
| Water (sufficient quantity to make up to 1,000 cm$^3$) | 338 g | 388 g | 354 g | 505 g |
| Average diameter of particles (in micrometers) | 2.8 | 3.1 | 3.4 | 3.2 |
| FC No. 4 | 33 s | 20 s | 40 s | 10 s |

EXAMPLES 9 to 11

Preparation of aqueous suspensions of atrazine

Following the procedure previously described, three aqueous suspensions of atrazine, whose respective compositions and properties are shown in Table 3 below (with the same abbreviations as in Table 1), were prepared.

As with the suspensions in Examples 1 to 4, all the suspensions in Examples 9 to 11 were stable:
more than 2 months at 45° C. and
more than 2 months in the temperature cycle 24 hours at +45° C., 24 hours at −5° C.

By diluting with water, suspensions were produced with 0.5% to 2% of active substance, without flocculation or sedimentation, during a period of use of about 24 hours.

TABLE 3

| Constituents of the suspension | Example 9 | Example 10 | Example 11 |
|---|---|---|---|
| Atrazine | 500 g | 450 g | 500 g |
| Sucroglycerides of copra, 10% in water | 100 g | 0 g | 0 g |
| Sucroglycerides of butter, 10% in water | 0 g | 100 g | 0 g |
| Sucroglycerides of tallow, 10% in water | 0 g | 0 g | 250 g |
| Ethoxylated castor oil (about 33 EO) | 5 g | 5 g | 5 g |
| Sodium dodecylbenzene-sulphonate | 2 g | 2 g | 2 g |
| Monopropylene glycol | 80 g | 80 g | 60 g |
| Xanthan gum, 2% in water | 50 g | 50 g | 50 g |
| Antifoam | 1 g | 1 g | 1 g |
| Water (sufficient quantity to make up to 1,000 cm$^3$) | 338 g | 380 g | 208 g |
| Average diameter of particles (in micrometers) | 3.0 | 3.3 | 3.5 |
| FC No. 4 | 20 s | 15 s | 17 s |

COMPARATIVE TEST B

Preparation of an aqueous suspension of atrazine

Following the procedure previously described, an aqueous suspension of atrazine, whose composition and properties are indicated below (with the same abbreviations as in Table 1), was prepared:

| | |
|---|---|
| atrazine | 500 g |
| phosphoric esters (mono- and di-) of ethoxylated tristyrylphenol (16 EO) neutralized with triethanolamine | 20 g |
| ethoxylated nonylphenol (10 EO) | 5 g |
| monopropylene glycol | 80 g |
| xanthan gum, 2% in water | 50 g |
| antifoam | 1 g |
| water to 1,000 cm³ | 420 g |
| Average diameter of particles (in micrometers) | 3.6 |
| FC No. 4 | 18 s |

As with the suspensions in Examples 1 to 4, the suspension of test B was stable:
more than 2 months at 45° C. and
more than 2 months in the temperature cycle 24 hours at +45° C., 24 hours at −5° C.

By diluting with water, suspensions were produced with 0.5% to 2% of active substance, without flocculation or sedimentation, during a period of use of about 24 hours.

It should be noted that using the compositions in accordance with the invention, containing nontoxic and biodegradable sucroglycerides, the same stability can be obtained at high concentration of active substance as with the best prior art suspensions.

EXAMPLES 12 to 15

Preparation of aqueous suspensions of diuron

Diuron is a known herbicide, with a melting point of 158° C. and a solubility in water at 25° C. of 0.042 g/l:

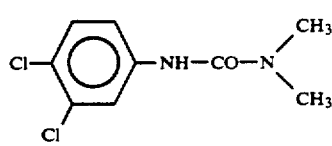

Following the procedure previously described, four suspensions of diuron, whose respective compositions are shown in Table 4 below (with the same abbreviations as in Table 1), were prepared in accordance with the invention.

As with the suspensions in Examples 1 to 4, all the suspensions in Examples 12 to 15 were stable:
more than 2 months at 45° C. and
more than 2 months in the temperature cycle 24 hours at +45° C., 24 hours at −5° C.

By diluting with water, suspensions were produced with 0.5% to 2% of active substance, without flocculation or sedimentation, during a period of use of about 24 hours.

TABLE 4

| Constituents of the suspension | Example 12 | Example 13 | Example 14 | Example 15 |
|---|---|---|---|---|
| Diuron | 600 g | 600 g | 600 g | 550 g |
| Sucroglycerides of castor oil 10% in water | 100 g | 150 g | 150 g | 100 g |
| Ethoxylated castor oil (about 33 EO) | 5 g | 8 g | 11 g | 5 g |
| Ethoxypropoxylated nonylphenol | 0 g | 0 g | 0 g | 2 g |
| Ethoxylated nonylphenol (about 12 EO) | 0 g | 3 g | 0 g | 0 g |
| Ethoxylated nonylphenol (about 8 EO) | 5 g | 0 g | 0 g | 0 g |
| Ethoxylated nonylphenol (about 1 EO) | 0 g | 0 g | 3 g | 3 g |
| Dioctyl sodium sulphosuccinate | 0 g | 0 g | 1 g | 0 g |
| Monopropylene glycol | 70 g | 70 g | 70 g | 70 g |
| Xanthan gum, 2% in water | 50 g | 50 g | 50 g | 50 g |
| Antifoam | 1 g | 1 g | 1 g | 1 g |
| Water (sufficient quantity to make up to 1,000 cm³) | 370 g | 318 g | 314 g | 402 g |
| Average diameter of particles (in micrometers) | 3.8 | 3.7 | 3.5 | 3.3 |
| FC No. 4 | 35 s | 30 s | 28 s | 27 s |

EXAMPLES 16 to 20

Preparation of aqueous suspensions of diuron

Following the procedure previously described, five aqueous suspensions of diuron, whose respective compositions are shown in Table 5 below (with the same abbreviations as in Table 1), were prepared in accordance with the invention.

As with the suspensions in Examples 1 to 4, all the suspensions in Examples 16 to 20 were stable:
more than 2 months at 45° C. and
more than 2 months in the temperature cycle 24 hours at +45° C., 24 hours at −5° C.

By diluting with water, suspensions were produced with 0.5% to 2% of active substance, without flocculation or sedimentation, during a period of use of about 24 hours.

TABLE 5

| Constituents of the suspension | Example 16 | Example 17 | Example 18 | Example 19 | Example 20 |
|---|---|---|---|---|---|
| Diuron | 600 g | 580 g | 640 g | 640 g | 640 g |
| Sucroglycerides of copra oil, 10% in water | 150 g | 145 g | 140 g | 140 g | 140 g |
| Ethoxylated castor oil (about 33 EO) | 5 g | 0 g | 0 g | 5 g | 5 g |
| Ethoxylated castor oil (about 18 EO) | 0 g | 5 g | 5 g | 0 g | 0 g |
| Ethoxylated nonylphenol (about 10 EO) | 5 g | 3 g | 4 g | 5 g | 3 g |
| Ethoxylated $C_{11}$ fatty acid (about 7 EO) | 0 g | 0 g | 0 g | 0 g | 5 g |
| Sodium dodecylbenzene sulphonate | 3 g | 3 g | 2 g | 0 g | 0 g |
| Dioctyl sodium sulphosuccinate | 0 g | 0 g | 0 g | 2 g | 0 g |
| Monopropylene glycol | 70 g | 70 g | 60 g | 60 g | 60 g |
| Xanthan gum, 2% | 50 g | 50 g | 40 g | 40 g | 40 g |

TABLE 5-continued

| Constituents of the suspension | Example 16 | Example 17 | Example 18 | Example 19 | Example 20 |
|---|---|---|---|---|---|
| in water | | | | | |
| Antifoam | 1 g | 1 g | 1 g | 1 g | 1 g |
| Water (sufficient quantity to make up to 1,000 cm³) | 316 g | 336 g | 321 g | 320 g | 319 g |
| Average diameter of particles (in micrometers) | 3.5 | 3.6 | 3.8 | 3.7 | 3.5 |
| FC No. 4 | 30 s | 35 s | 40 s | 40 s | 38 s |

EXAMPLES 21 and 22

Preparation of aqueous suspensions of diuron

Following the procedure previously described, two aqueous suspensions of diuron, whose respective compositions are shown in Table 6 below (with the same abbreviations as in Table 1), were prepared in accordance with the invention.

As with the suspensions in Examples 1 to 4, all the suspensions in Examples 21 to 22 were stable:
more than 2 months at 45° C. and
more than 2 months in the temperature cycle 24 hours at +45° C., 24 hours at −5° C.

By diluting with water, suspensions were produced with 0.5% to 2% of active substance, without flocculation or sedimentation, during a period of use of about 24 hours.

TABLE 6

| Constituents of the suspension | Example 21 | Example 22 |
|---|---|---|
| Diuron | 430 g | 450 g |
| Sucroglycerides of copra oil, 10% in water | 120 g | 0 g |
| Sucroglycerides of butter oil, 10% in water | 0 g | 100 g |
| Ethoxylated castor oil (about 33 EO) | 5 g | 10 g |
| Ethoxylated castor oil (about 18 EO) | 5 g | 0 g |
| Sodium dodecylbenzenesulphonate | 5 g | 5 g |
| Monopropylene glycol | 70 g | 70 g |
| Xanthan gum, 2% in water | 60 g | 60 g |
| Antifoam | 1 g | 1 g |
| Water (sufficient quantity to make up to 1,000 cm³) | 447 g | 455 g |
| Average diameter of particles (in micrometers) | 3.2 | 3.5 |
| FC No. 4 | 10 s | 12 s |

EXAMPLES 23 and 24

Preparation of aqueous suspensions of triflumizole

Triflumizole is a known fungicide, with a melting point of 63° C. and a solubility in water at 25° C. of 0.012 g/l:

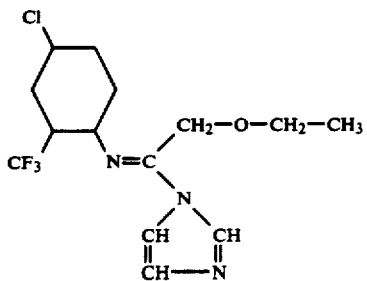

Following the procedure previously described, two aqueous suspensions of triflumizole, whose respective compositions are shown in Table 7 below (with the same abbreviations as for Table 1) were prepared in accordance with the invention.

As with the suspensions in Example 1 to 4, all the suspensions in Examples 23 and 24 were stable:
more than 2 months at a temperature lower than 35° C. (maximum temperature for the stability of the active substance).

By diluting with water, suspensions were produced with 0.5% to 2% of active substance, without flocculation or sedimentation, during a period of use of about 24 hours.

TABLE 7

| Constituents of the suspension | Example 23 | Example 24 |
|---|---|---|
| Triflumizole | 430 g | 500 g |
| Sucroglycerides of tallow, 10% in water | 130 g | 0 g |
| Sucroglycerides of castor oil, 10% in water | 0 g | 200 g |
| Ethoxylated castor oil (about 33 EO) | 8 g | 20 g |
| Sodium dodecylbenzenesulphonate | 3 g | 0 g |
| Sodium lauryl sulphate | 0 g | 3 g |
| Monopropylene glycol | 60 g | 70 g |
| Xanthan gum, 2% in water | 50 g | 50 g |
| Antifoam | 1 g | 1 |
| Water (sufficient quantity to make up to 1,000 cm³) | 374 g | 220 g |
| Average diameter of particles (in micrometers) | 4.2 | 4.5 |
| FC No. 4 | 39 s | 46 s |

We claim:

1. A concentrated aqueous suspension of a solid active substance, comprising:
   a solid active substance, sucroglycerides, at least one compound selected from the group consisting of an alkoxylated triglyceride, an alkoxylated fatty acid, a sorbitan ester, and an alkoxylated sorbitan ester, and water,
   wherein said solid active substance has a melting point greater than or equal to 45° C. and is substantially insoluble in water.

2. The suspension according to claim 1, further comprising:
   a wetting agent selected from the group consisting of anionic salts of surface-active agents, alkoxylated alcohols, substituted or non-alkoxylated phenols, silicone-based surface-active agents and fluorinated surface-active agents.

3. The suspension according to claim 1, wherein the sucroglycerides are prepared by transesterification of triglycerides with sucrose.

4. The suspension according to claim 3, wherein the triglycerides are natural and are selected from the group consisting of lard, tallow, groundnut oil, butter oil, cottonseed oil, linseed oil, olive oil, palm oil, grapeseed oil, fish oil, soybean oil, castor oil, colza oil, copra oil, and coconut oil.

5. The suspension according to claim 1, wherein the sucroglycerides are obtained from palm oil, lard, copra oil, tallow, colza oil, or castor oil.

6. The suspension according to claim 1, further comprising a phospholipid.

7. The suspension according to claim 6, wherein the phospholipid is selected from the group consisting of crude lecithins of plant or animal origin and lecithin fractions.

8. The suspension according to claim 6, comprising from 0.1% to 5% by weight of sucroglycerides and phospholipid, relative to the total volume of the suspension.

9. The suspension according to claim 6, wherein the weight ratio of sucroglycerides to phospholipid is 3:1 to 1:3.

10. The suspension according to claim 1, wherein the solid active substance is selected from the group consisting of deltamethrin, propham, tetramethrin, furalaxyl, heptachlor, propanil, oxadiazon, triflumizole, dimethametryn, atrazine, diuron, neburon, linuron, isoproturon, simazine, ametryne, phenmedipham, and pendimethalin.

11. The suspension according to claim 1, comprising from 30% to 90% by weight of said solid active substance, relative to the total volume of the suspension.

12. The suspension according to claim 1, wherein said at least one compound is selected from the group consisting of ethoxylated triglyceride, an ethoxylated fatty acid, a sorbitan ester, and an ethoxylated sorbitan ester.

13. The suspension according to claim 1, comprising from 0.1% to 3% by weight of said at least one compound selected from the group consisting of alkoxylated triglyceride, alkoxylated fatty acid, sorbitan ester, and alkoxylated sorbitan ester per volume of the suspension.

14. The suspension according to claim 1, further comprising at least one wetting agent selected from the group consisting of anionic salts of surface-active agents, alkoxylated alcohols and alkoxylated alkylphenols which are represented by the following formulas:

$R_1-SO_3-M$ $R_2-SO_4-M$ $R_3-(EO)_n-H$ $R_3-(PO)_n-H$ $R_3-(EO-PO)_n-H$ $R_4-COONa$ where:
$R_1$ represents
an alkylphenyl radical,
an alkyl radical, or
a 1,2-bis(octyloxycarbonyl)ethyl radical,
$R_2$ represents
an alkyl radical,
an ethoxylated alkylphenol radical, or
an ethoxylated alkyl radical,
$R_3$ represents
an alkylaryl radical, or
an alkyl radical having from 8 to 20 carbon atoms,
n is a number from 4 to 12,
$R_4$ represents an alkyl radical having 10 to 22 carbon atoms,
M represents Na, K, NH$_4$ or a triethanolammonium cation.

15. The suspension according to claim 1, further comprising at least one wetting agent selected from the group consisting of a silicone-based surface-active agent and a fluorinated surface-active agent.

16. The suspension according to claim 1, further comprising from 0.05% to 1% by weight of a wetting agent relative to the total volume of the suspension.

17. The suspension according to claim 7, wherein said crude lecithins are soybean lecithins or egg yolk lecithins.

18. The suspension according to claim 8, comprising 0.2% to 4% by weight of sucroglycerides and phospholipid, relative to the total volume of the suspension.

19. The suspension according to claim 11, comprising from 40% to 85% by weight of said solid active substance, relative to the total volume of the suspension.

20. The suspension according to claim 13, comprising from 0.2% to 2.8% by weight of said at least one compound per volume of the suspension.

21. The suspension according to claim 14, wherein $R_1$ is dodecylphenyl, dodecyl, or 1,2 bis (2-ethylhexyloxycarbonyl) ethyl.

22. The suspension according to claim 14, wherein $R_2$ is dodecyl or ethoxylated nonylphenol with 2 to 50 EO units.

23. The suspension according to claim 14, wherein $R_3$ is nonylphenyl, alkylnaphthyl or alkyl radicals having 10 to 14 carbon atoms.

24. The suspension according to claim 15, wherein said silicone-based surface-active agent is selected from the group consisting of copolymers of (1) polydimethylsiloxane and (2) either a homopolymer of ethylene glycol or copolymers of ethylene glycol and propylene glycol.

25. The suspension according to claim 15, wherein said fluorinated surface-active agent is selected from the group consisting of compounds containing a linear perfluorocarbon chain and a hydrophilic region.

26. The suspension according to claim 25, wherein said linear perfluorocarbon chain is hydrophobic or oleophobic, and said hydrophilic region contains an acidic or neutralized sulphonic group, a carboxylic group or an ethoxylated alcohol radical.

27. The suspension according to claim 16, comprising from 0.1% to 0.8% weight of wetting agent relative to the total volume of the suspension.

28. The suspension according to claim 1, comprising from 0.1% to 5% by weight of sucroglycerides relative to the total volume of the suspension.

29. The suspension according to claim 28, comprising 0.2% to 4% by weight of surcroglycerides relative to the total volume of the suspension.

* * * * *

UNITED STATES PATENT AND TRADEMARK OFFICE
CERTIFICATE OF CORRECTION

PATENT NO. : 5,290,751

DATED : March 01, 1994

INVENTOR(S) : Jean-Francois FIARD et al.

It is certified that error appears in the above-identified patent and that said Letters Patent is hereby corrected as shown below:

TITLE PAGE, left hand column beneath "[22] Filed:" insert --Foreign Application Priority Data
   Dec. 10, 1990 [FR] France................90 15738--.

Signed and Sealed this

Fourteenth Day of March, 1995

*Attest:*

BRUCE LEHMAN

*Attesting Officer*    *Commissioner of Patents and Trademarks*